(12) United States Patent
Andre et al.

(10) Patent No.: US 8,216,556 B2
(45) Date of Patent: Jul. 10, 2012

(54) COLORING MATERIAL AND ITS USES, IN PARTICULAR IN THE FIELD OF COSMETICS, ESPECIALLY FOR MAKING UP THE SKIN AND SUPERFICIAL BODY GROWTHS

(75) Inventors: Patrice Andre, Neuville aux Bois (FR); Elodie Verdier, Mardié (FR); Michel Garcia, Lauris (FR)

(73) Assignee: LVMH Recherche, Saint Jean de Braye (FR)

( * ) Notice: Subject to any disclaimer, the term of this patent is extended or adjusted under 35 U.S.C. 154(b) by 225 days.

(21) Appl. No.: 12/706,863

(22) Filed: Feb. 17, 2010

(65) Prior Publication Data

US 2010/0209369 A1  Aug. 19, 2010

(30) Foreign Application Priority Data

Feb. 18, 2009 (FR) ..................................... 09 51048

(51) Int. Cl.
*A61K 8/00* (2006.01)
*A61K 8/81* (2006.01)
(52) U.S. Cl. ......................................... 424/61; 424/70.7
(58) Field of Classification Search .................. None
See application file for complete search history.

(56) References Cited

FOREIGN PATENT DOCUMENTS

| | | | |
|---|---|---|---|
| GB | 1 023 414 A | | 3/1966 |
| GB | 1 181 079 A | | 2/1970 |
| JP | 53016039 | | 2/1978 |
| JP | 62 151467 | | 7/1987 |
| JP | 02 298345 | | 12/1990 |
| WO | WO0155262 | * | 8/2001 |

OTHER PUBLICATIONS

Murray, "Clays," International University, Department of Geological Sciences, no month available, 2006, 1-34.

* cited by examiner

*Primary Examiner* — Tracy Vivlemore
*Assistant Examiner* — Jennifer Berrios
(74) *Attorney, Agent, or Firm* — Woodcock Washburn LLP

(57) ABSTRACT

The invention relates to a solid coloring material obtained by precipitation, in an aqueous medium, of the reaction product of an alkali metal silicate with a colored complex obtained by reaction, in aqueous solution, of a hydrolysable tannin or of a plant extract comprising it with a salt of a metal cation. The invention also relates to a cosmetic composition intended for making up the skin or superficial body growths comprising this coloring material. It also relates to a method for making up the skin or superficial body growths comprising the topical application of this cosmetic composition.

22 Claims, No Drawings

COLORING MATERIAL AND ITS USES, IN PARTICULAR IN THE FIELD OF COSMETICS, ESPECIALLY FOR MAKING UP THE SKIN AND SUPERFICIAL BODY GROWTHS

CROSS REFERENCE TO RELATED APPLICATION

This application claims the benefit of French Patent Application No. 0951048, filed Feb. 18, 2009, the entirety of which is incorporated herein.

TECHNICAL FIELD

The subject matter of the present invention is novel coloring materials and their use in compositions, in particular cosmetic compositions. The invention applies very particularly to the preparation of coloring cosmetic compositions, in particular intended for making up the skin or superficial body growths. It also applies to any type of coloring composition for other industrial fields, such as the field of foodstuffs, that of medicaments, inks, dyes, paints and products which can be applied in the field of graphic arts and of decoration in general.

BACKGROUND

In the context of the present invention, the expression "coloring material" denotes a substance which acts as dye in the medium into which it has been introduced or on the surface of the material or support to which it has been applied.

In the cosmetics field, use is very often made of coloring materials of natural or synthetic origin and of inorganic or organic chemical nature. They are used mainly to produce a coloring effect on the skin or superficial body growths, as is the case for makeup products. These coloring materials can, in particular, be of plant origin.

Plant dyes are transparent in a liquid medium. Mention is made, among those which can be used in cosmetics, of anthocyanins, carotenoids, curcumin, and chlorophylls. They can be used to simply color a composition, without any coloring effect on the skin or superficial body growths. However, if it is desired to use them in makeup products or more generally to color a surface, in order for the rendering of the colors on the skin or superficial body growths or the surface to be satisfactory, it is necessary to render them opaque. For this, they are rendered insoluble. The main technique for rendering plant dyes insoluble consists in fixing them to a solid substrate.

The coloring materials obtained in the solid form include "lakes". Usually composed of three elements: a dye, a substrate, for example alumina, and a cation which acts as precipitating agent, lakes are used in particular in the preparation of paints, transparent coatings and glazes. These lakes are also sometimes used to color food preparations but more rarely in cosmetic compositions.

The lakes of natural dyes which are the most widely used have been manufactured starting from various anthraquinone-comprising plants of the family of the Rubiaceae, an example of which is provided by common madder (*Rubia tinctorum* L.), from some anthraquinone-rich insects or from a few other plants rich in flavonoids, neoflavonoids and other dyes of the same type (yellow lakes of mignonette and various Moraceae, purple lakes of logwood, pink and red lakes of woods from various members of the Caesalpiniaceae, and the like).

The conventional process for manufacturing a natural dye lake consists in bringing together a colored or uncolored aqueous extract originating from a vegetable, mineral or animal source and a metal salt, for example an aluminum salt in the form of a sulfate or of a chloride, in order to form a colored organometallic complex, and in precipitating said complex thus formed by addition of a cation in the form, for example, of a sodium, potassium or calcium salt.

Within the meaning of the invention, a "lake" is thus defined as a colored solid formed by precipitation, using a cation, of a colored organometallic complex formed in particular by addition of a metal cation to an aqueous extract.

"Complex" is understood to mean, in the present description, the product resulting from the combination of a metal cation with a ligand of organic nature.

The coloring of the complex may result from the use of a colored aqueous extract or else may appear only at the time of the complexing reaction with the metal cation. This coloring can vary according to the metal cation chosen for the preparation of the complex.

The molecules capable of forming colored organometallic complexes include the molecules belonging to the family of the tannins.

The tanning industry makes use of their natural affinity for various metal salts in preparing leather and hides (leather with tannin retreated with magnesium salts in particular).

Tannin/iron complexes have also been used since time immemorial in the form of fluid inks or for various applications in the field of the dyeing of textiles.

Tannins are found in most plants and in all their parts, in particular the bark, roots or leaves.

These tannins are polyphenolic acid derivatives which result from the esterification by these acids of the alcohol functional groups of sugars. They have a highly variable chemical structure but one which always comprises a polyphenolic part.

Standing out among the tannins are hydrolysable tannins, which are esters formed by reaction of a natural catechic acid, such as gallic acid, caffeic acid or ferulic acid, or of one of their oligomers or polymers, such as pentagalloylgallic, dehydrodigallic, ellagic, chebulic, hexahydroxydiphenic, nonahydroxytriphenic, valoneic, sanguisorbic, trilloic or gallagic acid, with a natural alcohol, generally a polyol, such as sugars (glucose, rhamnose, rutinose, fructose, galactose, mannose), inositol, quinic acid or shikimic acid.

These hydrolysable tannins can be:

monoesters, such as glucogallin, theogallin or chlorogenic acid;

polyesters, such as pentagalloylglucose, hexagalloylglucose, geranins, geranamines, tanic acids, tellimagrandins, casuarictin or pedunculagin;

oligomers of these polyesters, such as gemins, rugosins, isorugosins, cornusiins, coriarins, oenotheins, agrimonin, sanguins, corilagin, granantins and the other hydrolysable tannins isolated by the authors cited in the work "Plant Polyphenols: Vegetable Tannins Revisited", Haslam E., published by CUP Archive, in particular chapter 3, pages 90-153.

Mention is in particular made, among hydrolysable tannins, by way of example and without being limiting, of:

gallic tannins (or gallotannins), which are esters of gallic acid and of digallic acid with $C_5$ or $C_6$ sugars, such as glucose, or derivatives, such as hamamelose, ribose derivatives, ellagic tannins (or ellagitannins), which are esters of ellagic acid.

Hydrolysable tannins are not naturally colored but result in colored substances by the processes already explained, particularly with iron, with which they form a complex which is black in color.

However, dye lakes based on organometallic complexes comprising hydrolysable tannins are not used to any great extent as they exhibit a mediocre stability. In particular, lakes of gallic tannins and of iron have not been developed, in particular because the tannins/iron complex with a black color is very difficult to precipitate and at the same time very unstable, with a tendency to redissolve. Reference is made, in this case, to a "delaking" phenomenon.

In order to be in a position to use a dye lake based on hydrolysable tannins and metal salts in compositions, in particular cosmetic compositions, especially in makeup products, it is essential to stabilize it in order to prevent a detrimental change in the color over time, by a delaking phenomenon, and a detrimental change in the intrinsic properties of these compositions.

To date, there does not exist any stabilized lake based on hydrolysable tannins, neither does there exist a solid coloring material manufactured from plant extracts comprising such hydrolysable tannins, the stability of which allows them to be used as a formulation ingredient.

It is precisely the problem of the stabilization of dye lakes based on hydrolysable tannins and metal cations which the present invention intends to solve. Within the meaning of the invention, a dye lake is stable when it does not exhibit any delaking phenomenon, that is to say any dissolution of the colored complex when the lake is suspended in a solvent normal in the field of application, or detrimental change in color, in particular after prolonged exposure to a light source.

SUMMARY

Solid coloring materials for use in cosmetics and other coloring applications are described. These solid coloring materials are prepared by precipitation, in an aqueous medium, of a reaction product of an alkali metal silicate with a colored complex, the colored complex obtained by reaction, in aqueous solution, of at least one hydrolysable tannin, or of a plant extract comprising at least one hydrolysable tannin, with a salt of a metal cation.

DETAILED DESCRIPTION OF ILLUSTRATIVE EMBODIMENTS

The research carried out by the inventors of the present invention has made it possible to obtain dye lakes based on hydrolysable tannins which are stable, in particular with regard to delaking, which makes it possible to use them as coloring material in the preparation of coloring compositions in numerous industrial fields, in particular of cosmetic compositions.

The stabilization of said lake results from the fixing of said colored complex based on hydrolysable tannins and at least one metal cation to a very specific solid substrate which makes it possible to render said colored complex insoluble, while avoiding any phenomenon of delaking and of detrimental change in the color of the colored complex rendered insoluble.

Thus, according to a first subject matter, the invention relates to a novel solid coloring material.

According to the essential characteristic of this first subject matter, this solid coloring material is obtained by precipitation, in an aqueous medium, of the reaction product of an alkali metal silicate with a colored complex obtained by reaction, in aqueous solution, of at least one hydrolysable tannin or of a plant extract comprising it with a salt of a metal cation.

According to a second subject matter, the invention relates to the process for the manufacture of the coloring material of the first subject matter.

According to its essential characteristic, this process comprises:
  a stage of rendering insoluble a colored complex as defined above by reaction, in an aqueous medium, of said colored complex with an alkali metal silicate, in order to precipitate said coloring material, and
  a stage of recovery of said coloring material.

According to a third subject matter, the invention relates to a cosmetic composition intended for making up the skin or superficial body growths comprising the coloring material of the first subject matter or obtained according to the second subject matter.

According to a fourth subject matter, the invention relates to the use of the coloring material of the first subject matter or obtained according to the process of the second subject matter in the preparation of a coloring composition.

According to a final subject matter, the invention relates to a method for making up the skin or superficial body growths comprising the topical application of a composition comprising a coloring material as defined above.

Other characteristics and advantages of the invention will become apparent in the detailed description which follows.

As set out above, the invention results from the discovery, made by the inventors, that it is possible to obtain a stable lake starting from a colored complex based on at least one hydrolysable tannin, which occurs bound to a solid substrate formed by reaction of an alkali metal silicate with this colored complex.

The silicate participating in the preparation of the coloring material of the invention can be any alkali metal silicate. However, the choice is preferably to be made of sodium silicate, potassium silicate or lithium silicate and preferably of sodium silicate.

As is known in the literature, the metal cation forming the colored complex by fixing with hydrolysable tannins can be chosen within a wide range. Advantageously, this cation is chosen from the group consisting of iron, aluminum, magnesium, calcium and titanium. Preferably, the choice is made of ferrous ($Fe^{2+}$) iron.

The hydrolysable tannin is preferably an ellagic tannin or a gallic tannin. The colored complexes of hydrolysable tannins are already well known in the literature. However, the choice is particularly preferably made of the colored complexes which are black in color in which the metal cation is ferrous iron. Such colored complexes are known.

According to a preferred alternative form of the invention, use is made, in the preparation of the coloring materials of the invention, of colored complexes obtained from plant extracts comprising hydrolysable tannins, in particular aqueous solutions of such extracts including these hydrolysable tannins. The extracts used in the preparation of the colored complex are advantageously aqueous extracts.

Generally, the colored complex is more particularly formed by the reaction, in aqueous solution, of at least one hydrolysable tannin or a plant extract comprising it and of iron.

When the hydrolysable tannins are obtained by extraction starting from a plant material, all the methods which make it possible to extract tannins can be used, in particular those listed by Haslam in his abovementioned work and in the references which are cited therein.

Extraction is carried out in particular by pressing, maceration, decoction or steeping using a polar solvent or a mixture of polar solvents.

The polar solvent is chosen in particular from glycols, alcohols or water, or their mixtures, in particular from aqueous/alcoholic mixtures.

The extraction of hydrolysable tannins from plant tissues can be improved by the application of ultrasound.

The plant extract obtained can be used directly or else can be treated, for example by removing the extraction solvent, in order to obtain a dry extract.

As is known in the literature, plant extracts comprising hydrolysable tannins can be obtained from whole plants comprising them or from various aerial or underground parts of the same plants, such as the leaves, branches, flowers, roots, bark, fruits, seeds or also outgrowths due to attack by parasite or to infection by pathogenic agent, generally known by the generic term of "galls."

According to an advantageous alternative form, the plant extract is obtained from an aerial part of a plant comprising at least one hydrolysable tannin and in particular from the bark.

According to a particularly advantageous alternative form of the invention, the plant is chosen from the family of the Combretaceae.

According to a very particularly advantageous alternative form, the plant is chosen from those belonging to the *Anogeissus* genus, for example from the plant species *Anogeissus leiocarpus, Anogeissus latifolia* or *Anogeissus acuminata*, preferably *Anogeissus leiocarpus.*

The leaves of the plant *Anogeissus leiocarpus* have already been used in dyeing, in combination with ferruginous muds, in the creation of patterned cotton fabrics; this is the "bogolan" style.

For the present invention, use is preferably made of an extract of bark of a plant belonging to the *Anogeissus* genus.

According to a particularly preferred implementation of the present invention, use is made of an extract of bark of the plant *Anogeissus leiocarpus.*

The color of the coloring material depends essentially on the nature of the metal cation but can in addition vary according to the conditions of the complexing reaction or of the precipitation reaction.

According to an advantageous alternative form of the invention, a complex which is black in color is obtained starting from hydrolysable tannins present in an *Anogeissus leiocarpus* extract, for example obtained by extraction of bark of said plant in the aqueous phase, and from iron in the form of $Fe^{2+}$ ions. Starting from this colored complex, the coloring material thus formed is black in color.

According to an advantageous alternative form of the invention, the coloring material is in the form of a pulverulent solid, preferably a pulverulent solid which is black in color.

As set out above, the process for preparing the coloring material of the invention consists in rendering the colored complex insoluble by reaction, in an aqueous medium, of said colored complex with an alkali metal silicate, which makes it possible to precipitate the coloring material in the powder form, and in then recovering this coloring material.

The colored complex used to carry out this precipitation stage is advantageously obtained by addition of a salt of a metal cation to an aqueous solution comprising at least one hydrolysable tannin or a plant extract comprising it.

Thus, according to a preferred alternative form of the invention, the process of the invention comprises a first stage of preparation of a colored complex as described above by addition of a salt of a metal cation, preferably an iron sulfate, to an aqueous solution comprising at least one hydrolysable tannin or a plant extract comprising it.

Said aqueous solution is advantageously obtained by dissolution, in water, of a plant extract as defined above, in particular of an *Anogeissus leiocarpus* extract.

According to an advantageous alternative form, the colored material is obtained from an aqueous solution of a plant extract comprising hydrolysable tannins obtained by aqueous extraction. This aqueous extraction stage is advantageously carried out using an ultrasonic extractor.

The stage of rendering the colored complex insoluble is preferably carried out by formation of an aqueous suspension of particles which are obtained by reaction, in an aqueous medium, of the colored complex with an alkali metal silicate.

This stage of rendering insoluble is advantageously carried out by stirring the aqueous solution of colored complex with an aqueous solution of an alkali metal silicate, the mixture reacting during the contacting operation in order to precipitate said colored solid particles in situ.

The water-soluble alkali metal silicate is preferably sodium silicate.

According to this process, a suspension of colored solid particles to which the colored complex defined above is fixed is prepared, said suspension being obtained by forming the colored solid particles in situ in the aqueous solution of a colored complex, in particular by reaction, in an aqueous medium, of said colored complex with an alkali metal silicate, for example a sodium silicate.

These particles are subsequently recovered during a final stage.

The colored solid particles are recovered by removing the aqueous medium by any appropriate solid/liquid separation means.

The process thus advantageously comprises at least one stage of separation by settling and/or of washing and/or of filtration and/or of drying and/or of spraying or of atomization intended to collect a powder formed of coloring material essentially composed of the solid substrate to which the colored complex is fixed.

A person skilled in the art can vary the various operating conditions and parameters. However, it should be noted that the choice of the temperature makes it possible to act on the kinetics of the reaction for rendering insoluble and also on the composition of the support, which is not without effect on the coloring of the final coloring material. Thus, it could be observed that the "black" is more intense when the tannin/iron colored complex is treated under cold conditions, for example at approximately 4° C.

According to a preferred implementation of the process of the invention in which a coloring material which is black in color is prepared from a tannin/iron colored complex, said material is prepared by the following stages:

a stage of preparation of a colored complex by addition of an iron salt, preferably a ferrous iron sulfate, to an aqueous solution of an extract of plants belonging to the *Anogeissus* genus, preferably of an extract of bark of *Anogeissus leiocarpus,* a stage of in situ precipitation of said colored complex by bringing said aqueous solution of colored complex into contact, with stirring, with an aqueous solution of an alkali metal silicate, preferably sodium silicate.

According to a preferred implementation, a water-soluble iron salt is added, at least 20% by weight, with respect to the weight of dry plant extract employed.

According to a preferred implementation, the alkali metal silicate is added in a proportion substantially equal to the weight of the iron salt, i.e. at least 20% by weight, with respect to the weight of dry plant extract employed.

The coloring materials of the invention are of particular use in cosmetic compositions and in particular in cosmetic compositions intended for making up the skin or superficial body growths.

Thus, the invention relates to coloring composition, in particular cosmetic compositions for making up the skin or superficial body growths, comprising the coloring material as defined above.

Within the meaning of the invention, the coloring compositions are those in which the coloring agent retains its coloring properties without the other compounds denaturing the specific structure thereof.

In the field of cosmetics, the coloring composition will generally be a product for making up the skin or superficial body growths, in particular a mascara, a foundation, an eye shadow, an eyeliner, a nail varnish or a loose or compact powder.

The cosmetic compositions comprising the coloring material of the invention can comprise at least one cosmetically acceptable active agent and at least one cosmetically acceptable excipient chosen in particular from pearlescent agents, polymers, surface-active agents, rheology agents, fragrances, electrolytes, pH adjusters, antioxidants, preservatives, their mixtures and optionally other coloring agents.

The invention also relates to the use of said coloring material, in particular obtained according to the process described above, in the preparation of a coloring composition, in particular of a cosmetic composition for making up the skin or superficial body growths, especially the eyelashes or nails.

The invention relates in particular to the use of the black coloring material prepared from an extract of bark of *Anogeissus leiocarpus* as coloring agent in coloring compositions capable of including it and more particularly in cosmetic compositions, in particular compositions intended for making up the skin or superficial body growths, especially the eyelashes or nails.

A person skilled in the art easily understands that the amount of coloring material present in the compositions of the invention depends very largely on the type of composition and on the effect desired.

Finally, the invention relates to a method for making up the skin or superficial body growths, in particular the eyelashes or nails, comprising the application, to at least a portion of the skin or superficial body growths, of a composition as described above.

As set out above, the coloring materials of the invention also have applications in fields other than that of cosmetics, in particular in that of foodstuffs or decorative paint.

Other aims, characteristics and advantages of the invention will become clearly apparent in the light of the examples, which are given by way of illustration and should thus in no way limit the scope of the invention.

EXAMPLE 1

Preparation of a Dye Lake Based on Hydrolysable Tannins, and Study of its Stability 1—Preparation of the Dye Lake A starting material composed of bark of Anogeissus leiocarpus collected in Burkina Faso was milled and then sieved in order to obtain a coarse powder, the size of which was less than 1 mm.

This plant starting material was extracted for 30 minutes at 60° C. in an ultrasonic extractor at a frequency of 27 kHz. After filtration, the solid residue was extracted a second time under the same conditions.

The two filtered liquors were combined and a solution of ferrous sulfate in water was added thereto, at 20% by weight of ferrous sulfate, with respect to the weight of powdered bark used in the extraction.

After cooling to 20° C., an approximately 40% by weight sodium silicate solution, diluted in 3 times its volume of water, was added with stirring. The flakes of precipitated coloring material appearred in the solution.

After separation by settling and removal of the supernatant, the precipitate was washed twice with osmosed water. The precipitate, formed of solid particles which were black in color, was subsequently filtered off, then dried, then again washed, this time with a 60° solution of ethanol in water, and finally dried once again.

2—Study of the Stability of the Lake

The lake obtained above was subjected to tests targeted at evaluating its stability.

a) Stability in Various Media

In order to study the appearance of a possible phenomenon of delaking, the lake was suspended in standard solvents in order to confirm the absence of reversible dissolution of the tannins/iron complex.

The procedure for visualizing the delaking in the dispersion medium is as follows:

0.1 g of lake prepared above and 9.9 g of solvent are weighed out. Stirring was carried out at ambient temperature for 20 minutes. The solvents tested were ethanol, ethyl acetate, pentacyclomethicone, glycerol or glycerol tricaprate/caprylate (Miglyol®, Prodasynth SAS, France). Centrifuging was carried out at 4500 rev/min for 45 min in order to separate the treated lake particles.

Delaking was reflected by a coloring of the supernatant recovered after centrifuging.

Results:

No delaking was observed at 20° C., whatever the solvent tested (colorless supernatant).

This test on the stability of the dispersions was repeated at 80° C., in water and in a liquid paraffin.

Results:

No delaking of the lake particles was observed at a 1% by weight suspension in liquid paraffin. Likewise, no delaking of the lake particles was observed at a 1% by weight suspension in water.

On the strength of these results, the stability of the lake is acceptable with regard to various dispersion media commonly used in cosmetics.

b) Stability Toward Light and UV Radiation

Natural dyes are known for low stability toward light. The color produced by these dyes has a tendency to detrimentally change, reflecting physicochemical modifications which are harmful with regard to the effect produced visually.

In order to test its resistance to light and to UV radiation, a sample of the lake prepared above was subjected to a photooxidation test (1500 watts for 12 h) using a Heraeus Suntest® CPS+ device.

No variation in color was observed visually.

EXAMPLE 2

Makeup Composition Comprising a Coloring Material Based on a Tannin/Iron Complex The coloring material obtained according to example 1 was deep black in color. It was added to the fatty phase of a mascara formulation, the formulation of which is described below:

| | |
|---|---|
| Coloring material according to example 1 | 8 |
| Mascara excipients (including fragrances and preservatives) | q.s. |
| Water | q.s. 100 |

The mascara thus obtained was black in color.

What is claimed:

1. A cosmetic composition comprising a solid coloring material prepared by precipitation, in an aqueous medium, of a reaction product of an alkali metal silicate with a colored complex, the colored complex obtained by reaction, in aqueous solution, of at least one hydrolysable tannin, or of a plant extract comprising at least one hydrolysable tannin, with a salt of ferrous iron.

2. The cosmetic composition of claim 1, wherein said colored complex is black in color.

3. The cosmetic composition of claim 1, wherein said hydrolysable tannin is an ellagic or gallic tannin.

4. The cosmetic composition of claim 1, wherein said plant extract is an aqueous extract.

5. The cosmetic composition of claim 1, wherein said plant extract is obtained from an aerial part of a plant comprising hydrolysable tannins.

6. The cosmetic composition of claim 1, wherein said plant extract is obtained from bark.

7. The cosmetic composition of claim 1, wherein said plant belongs to the family Combretaceae.

8. The cosmetic composition of claim 1, wherein said plant belongs to the Anogeissus genus.

9. The cosmetic composition of claim 1, wherein said plant extract is an extract of Anogeissus bark.

10. The cosmetic composition of claim 8, wherein said plant belongs to the species Anogeissus leiocarpus.

11. The cosmetic composition of claim 1, wherein said alkali metal silicate is sodium silicate, potassium silicate or lithium silicate.

12. The cosmetic composition of claim 1, wherein the colored complex is obtained by a reaction of an aqueous solution of an extract of bark of the plant Anogeissus leiocarpus and ferrous iron.

13. The cosmetic composition of claim 1, wherein the coloring material is in the form of a powder which is black in color.

14. The cosmetic composition as claimed in claim 1, wherein the cosmetic composition is a mascara, a foundation, an eye shadow, an eyeliner, a nail varnish, a loose powder, compact powder, a paint, or a decorative paint.

15. The cosmetic composition as claimed in claim 12, wherein the cosmetic composition is a mascara, a foundation, an eye shadow, an eyeliner, a nail varnish, a loose powder, compact powder, a paint, or a decorative paint.

16. A process for the preparation of a cosmetic composition of claim 1 comprising a coloring material as claimed in claim 1, comprising:

preparing a coloring material by rendering insoluble a colored complex, the colored complex obtained by reaction, in aqueous solution, of at least one hydrolysable tannin, or of a plant extract comprising at least one hydrolysable tannin, with a salt of ferrous iron, by reaction, in an aqueous medium, of said colored complex with an alkali metal silicate, in order to precipitate said coloring material, recovering said coloring material; and combining said coloring material with at least one cosmetically acceptable active agent and at least one cosmetically acceptable excipient to form the cosmetic composition.

17. The process as claimed in claim 16, wherein said plant extract is obtained by aqueous extraction.

18. The process as claimed in claim 16, wherein said plant extract is an Anogeissus extract.

19. A method for making up the skin or superficial body growths comprising topically applying a cosmetic composition as defined in claim 1.

20. The method of claim 19, wherein the colored complex of the cosmetic composition is obtained by a reaction of an aqueous solution of an extract of bark of the plant Anogeissus leiocarpus and of ferrous iron.

21. A method for making up the skin or superficial body growths, comprising topically applying a cosmetic composition prepared according to the process of claim 16.

22. The method of claim 21, wherein the colored complex of the cosmetic composition is obtained by a reaction of an aqueous solution of an extract of bark of the plant Anogeissus leiocarpus and of ferrous iron.

* * * * *